United States Patent [19]
Kampmann et al.

[11] Patent Number: 5,663,351
[45] Date of Patent: Sep. 2, 1997

[54] PROCESS FOR THE CONTINUOUS PREPARATION OF 2,2,6,6-TETRAMETHYLPIPERIDINE

[75] Inventors: Detlef Kampmann, Gersthofen; Georg Stuhlmüller, Gablingen, both of Germany

[73] Assignee: Hoechst Aktiengesellschaft, Germany

[21] Appl. No.: 352,558

[22] Filed: Dec. 8, 1994

[30] Foreign Application Priority Data

Dec. 11, 1993 [DE] Germany .................. 43 42 276.4

[51] Int. Cl.$^6$ .................................................. C07D 211/02
[52] U.S. Cl. ................................... 546/185; 546/244
[58] Field of Search ................................. 546/185, 244

[56] References Cited

U.S. PATENT DOCUMENTS 4,208,525  6/1980  Rasberger et al. ............... 546/184
4,252,958  2/1981  Hirai et al. ........................ 546/242

OTHER PUBLICATIONS

Nelson, J.L., et al, *Chem. Abs.* 44:7275d, "Studies on the mechanism of the von Braun reaction" (Aug. 25, 1950).
Bikova, N., et al, *Chem. Abs.* 56:10088d, "The synthesis of the ganglion–blocking preparation, Pempidin" (Apr. 30, 1962).

*Primary Examiner*—Alan L. Rotman
*Assistant Examiner*—Raymond Covington
*Attorney, Agent, or Firm*—Connolly & Hutz

[57] ABSTRACT

Process for the continuous preparation of 2,2,6,6-tetramethylpiperidine.

The reduction of triacetonamine with hydrazine also succeeds continuously by reactive distillation if the hydrazone is first formed and this is continuously transported to the distillation bottoms comprising a high-boiling solvent and an alkali at the base of a distillation column and the resulting 2,2,6,6-tetramethylpiperidine is distilled off as an azeotrope.

In this procedure a hydrazine/triacetonamine ratio of 1.5:1 to 2.0:1 is sufficient, in comparison with the conventional synthesis, the product yield being able to be considerably increased (>90%). Moreover, the amounts of alkali and solvent used can be considerably reduced.

18 Claims, No Drawings

PROCESS FOR THE CONTINUOUS PREPARATION OF 2,2,6,6-TETRAMETHYLPIPERIDINE

The invention relates to a continuous process for the preparation of 2,2,6,6-tetramethylpiperidine by reduction of 4-oxo-2,2,6,6-tetramethylpiperidine with hydrazine.

2,2,6,6-Tetramethylpiperidine is a product which is used for the most diverse purposes because of its strong basicity, for example as a light stabilizer for polyolefins, as a cocatalyst in olefin polymerizations (Ziegler catalysts), as a building block for the synthesis of pharmaceuticals and crop protection products, as a cocatalyst in the synthesis of dichloroacetyl chloride, to name some applications.

The 4-unsubstituted 2,2,6,6-tetramethylpiperidine is generally prepared from the corresponding 4-oxo compound.

It is known that triacetonamine can be converted by hydrazine to the hydrazone which is then cleaved in the presence of alkali into 2,2,6,6-tetramethylpiperidine and nitrogen (cf. CA; 44 7275 d, CA 56 10088 d). The described reduction with hydrazine is only carried out discontinuously, large amounts of solvents (approximately 11 mol of solvent/mol triacetonamine) and KOH (molar ratio 4:1) being required for the hydrazone cleavage. In addition, a molar hydrazine excess of 1:2–1:3 is required in order to achieve adequate yields (60 to 70%).

However, this previously known process for the reduction of triacetonamine is scarcely suitable for industrial application. The results are not in a reasonable relationship to the expense of the reduction.

It has now been found that the reduction of triacetonamine with hydrazine can also be carried out continuously by reactive distillation.

The process according to the invention is carried out in such a way that the hydrazone is first formed from triacetonamine by means of hydrazine hydrate. For this purpose, triacetonamine is mixed with stirring with 1.5 to 3 times the molar amount of hydrazine hydrate. The resulting solution of the hydrazone is transported to distillation bottoms at the base of a distillation column held at a temperature of 160° to 200° C. These distillation bottoms comprise a high-boiling solvent which predominantly contains OH groups, such as ethylene glycols and propylene glycols, and an alkali metal hydroxide, preferably KOH. The hydrazone cleavage proceeds spontaneously under these conditions. In addition to the nitrogen released, a mixture distills over which comprises 2,2,6,6-tetramethylpiperidine, water and hydrazine. The distillate divides into two phases after the condensation, the upper phase containing the 2,2,6,6-tetramethylpiperidine having a concentration of >90%. The lower phase contains excess hydrazine and water and only small amounts of the product of value.

In order to avoid foam formation in the distillation bottoms, 5 to 10% of paraffin are added, based on the solvent.

With this procedure, a hydrazine/triacetonamine ratio of 1.5:1 to 2.0:1 is sufficient, in comparison with the conventional synthesis, the product yield being able to be considerably increased (>90%). In addition to this advantage, the amounts of alkali and solvent used can be considerably decreased. The alkali/triacetonamine ratio in the discontinuous process is 4:1, in the continuous process according to the invention, based on the triacetonamine throughput rate, it is approximately 1:40 to 1:50. The improvements in solvent use are in a similar order of magnitude.

Further use of the distillation bottoms for hydrazone cleavage is possible without problem, the selectivity of the reaction decreasing, however, and the total yield being impaired. It is therefore preferred to replace some of the alkali/solvent mixture regularly.

EXAMPLE

Molten triacetonamine (approximately 50° C.) was introduced into a stirred vessel and 1.5 times the molar amount of hydrazine hydrate, based on the amount of triacetonamine, was added. The mixture heated in the course of this to 80° to 90° C. The hydrazone solution cooled to 40° to 50° C. was used for the subsequent reaction.

250 cm$^3$ of triethylene glycol (=279 g), 56.3 g of paraffin oil and 42.1 g of KOH were introduced into an apparatus composed of a 1 dm$^3$ four-neck flask having a Vigreux column (25 cm) which was provided with a water separator and intensive cooler. 2.5 to 3.5 cm$^3$ of the above hydrazone solution/min were pumped by means of a metering pump into these distillation bottoms which were kept at a temperature of 175° to 195° C. with vigorous stirring. The hydrazone was spontaneously cleaved under these reaction conditions. Together with the nitrogen released, a reaction mixture comprising 2,2,6,6-tetramethylpiperidine, water and hydrazine distilled off. The condensation product formed two phases which were removed collectively by the water separator and then separated. The organic phases obtained contained 90 to 95% of 2,2,6,6-tetramethylpiperidine.

The trial was terminated after a throughput of approximately 3300 g of hydrazone solution (approximately 1900 g of triacetonamine). The analyses of the organic phases gave a 2,2,6,6-tetramethylpiperidine yield of 91%. The combined organic phases were then fractionated by distillation. A product was obtained having a >99% purity.

We claim:

1. A process for the continuous preparation of 2,2,6,6-tetramethylpiperidine by reaction of triacetonamine with hydrazine and cleavage of the resulting hydrazone at a temperature of above 160° C., which comprises continuously transporting the hydrazone as an aqueous solution to the distillation bottoms which comprise a high-boiling solvent and an alkali at the base of a distillation column and distilling off as an azeotrope with water the resulting 2,2,6,6-tetramethylpiperidine and separating it from the water.

2. The process as claimed in claim 1, wherein the high-boiling solvent contains OH groups.

3. The process as claimed in claim 1, wherein the high-boiling solvent is a glycol.

4. A process for the continuous preparation of 2,2,6,6-tetramethylpiperidine from the corresponding 4-oxo-hydrazone, comprising continuously reactively distilling an alkaline solution containing said hydrazone, in a reactive distillation zone separate from any zone in which said alkaline solution is prepared, to obtain a distillate containing 2,2,6,6-tetramethylpiperidine, and recovering 2,2,6,6-tetramethylpiperidine from said distillate.

5. The process as claimed in claim 4, wherein said distilling step is carried out at a temperature between 160° and 200° C.

6. The method as claimed in claim 4, wherein said solution contains water and a high-boiling solvent containing OH groups.

7. The method as claimed in claim 6, wherein said solvent contains an ethylene glycol or a propylene glycol.

8. The method as claimed in claim 4, wherein said solution is made alkaline by an alkali metal hydroxide.

9. The method as claimed in claim 8, wherein said alkali metal hydroxide is KOH.

10. The method as claimed in claim 4, wherein said solution contains a foam-suppressing amount of a paraffin.

11. The method as claimed in claim 4, wherein said hydrazone is formed by reacting triacetonamine with hydrazine hydrate.

12. The method as claimed in claim 11, wherein the ratio of hydrazine hydrate to triacetonamine is between 1.5:1 to 3:1.

13. The method as claimed in claim 11, wherein the ratio of hydrazine hydrate to triacetonamine is between 1.5:1 to 2.0:1.

14. The method as claimed in claim 4, wherein the 2,2,6,6-tetramethylpiperidine-containing phase of said distillate contains at least 90% 2,2,6,6-tetramethylpiperidine.

15. A process for the continuous preparation of 2,2,6,6-tetramethylpiperidine, in a reactive distillation zone, from the hydrazone obtained from 4-oxo-2,2,6,6-tetramethylpiperidine, comprising:

obtaining, externally to said reactive distillation zone, an aqueous solution containing said hydrazone, continuously conveying said aqueous solution containing said hydrazone to the bottoms of said reactive distillation zone, said bottoms containing a high-boiling solvent containing OH groups and an alkali, continuously reactively distilling off an azeotrope containing 2,2,6,6-tetramethylpiperidine and water, and obtaining from said distilling step a 2,2,6,6-tetramethylpiperidine-containing first phase and an aqueous second phase, and separating said second phase from said first phase.

16. The process as claimed in claim 15, wherein said bottoms are maintained at a temperature in the range of 160° to 200° C., and said high-boiling solvent is a glycol.

17. The process as claimed in claim 15, wherein high boiling-solvent and alkali in said bottoms are periodically replaced.

18. The process as claimed in claim 15, wherein, after said separating step, the resulting separated, first phase is fractionally distilled.

\* \* \* \* \*